Figure 3:
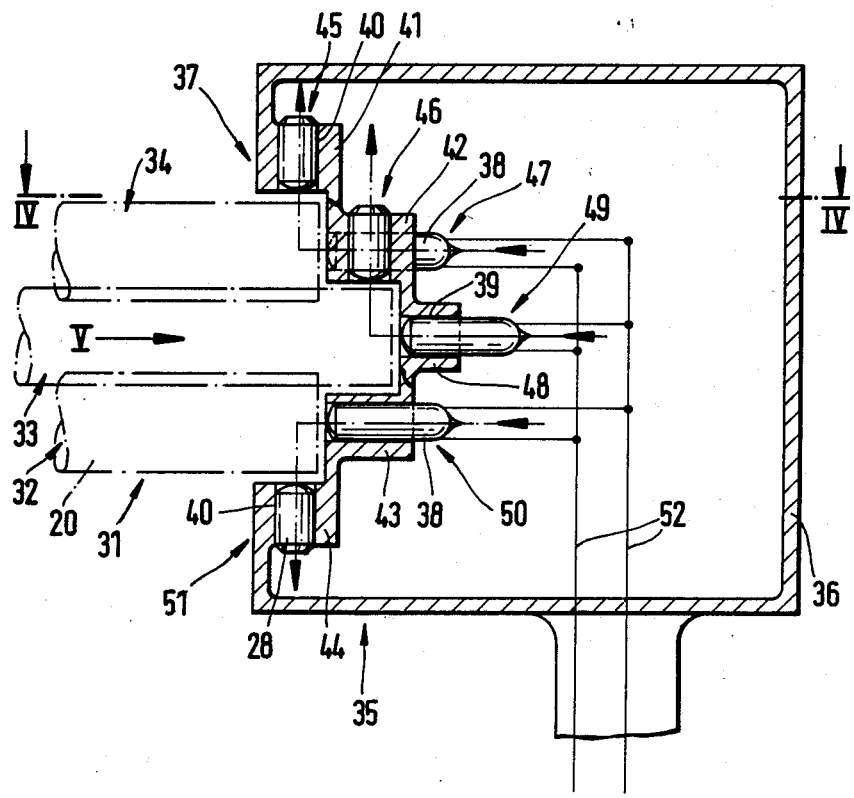

United States Patent [19]

Focke et al.

[11] Patent Number: 4,907,607
[45] Date of Patent: Mar. 13, 1990

[54] PROCESS AND DEVICE FOR TESTING CIGARETTES OR THE LIKE FOR FAULTS

[75] Inventors: Heinz Focke; Kurt Liedtke, both of Verden, Fed. Rep. of Germany

[73] Assignee: Focke & Company, Verden, Fed. Rep. of Germany

[21] Appl. No.: 545,717

[22] Filed: Oct. 26, 1983

[30] Foreign Application Priority Data

Nov. 23, 1982 [DE] Fed. Rep. of Germany ....... 3243204

[51] Int. Cl.[4] ............................ A24C 5/34; A24C 5/32
[52] U.S. Cl. ..................................... 131/280; 131/281; 131/906; 131/908; 250/223 R; 209/536
[58] Field of Search ............... 131/280, 281, 902, 906, 131/908; 250/223 R, 572; 209/536

[56] References Cited

U.S. PATENT DOCUMENTS

| | | | |
|---|---|---|---|
| 3,453,440 | 7/1969 | Muir et al. ............................ | 131/908 |
| 3,557,374 | 1/1971 | Schmermund ....................... | 131/908 |
| 3,557,375 | 1/1971 | Schmermund ....................... | 131/908 |
| 3,812,349 | 5/1974 | Gugliotta et al. ................... | 250/572 |

FOREIGN PATENT DOCUMENTS

| | | |
|---|---|---|
| 2653298 | 6/1977 | Fed. Rep. of Germany . |
| 2732520 | 1/1979 | Fed. Rep. of Germany . |
| 0142648 | 3/1978 | German Democratic Rep. . |
| 1347221 | 2/1974 | United Kingdom . |
| 2060348 | 5/1981 | United Kingdom ................ 131/908 |

Primary Examiner—V. Millin
Assistant Examiner—Joe H. Cheng
Attorney, Agent, or Firm—Sughrue, Mion, Zinn, Macpeak & Seas

[57] ABSTRACT

For testing cigarettes, a test head confronts end faces of the cigarettes. Light beams emitted by a light transmitter are transmitted through those cigarettes having a tobacco deficiency. The transmitted light exits from sides of the defective cigarettes and is received by a transversely arranged receiver responsive to light transmitted through the cigarette paper.

14 Claims, 6 Drawing Sheets

FIG. 1
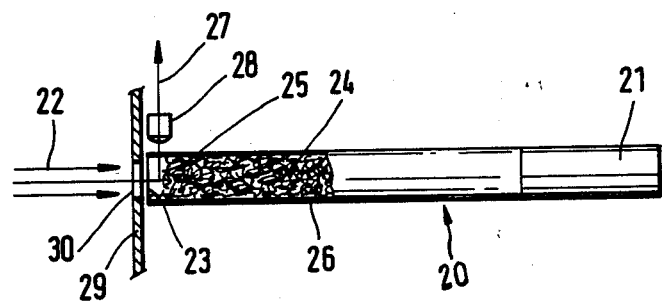
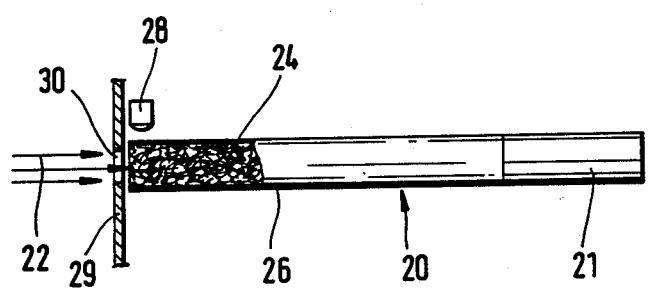
FIG. 2

PROCESS AND DEVICE FOR TESTING CIGARETTES OR THE LIKE FOR FAULTS

DESCRIPTION

The invention relates to a process for testing cigarettes or the like for faults as regards the presence of (sufficient) tobacco, cigarette filters, etc., by means of light which is directed onto the cigarette and is emitted by a light source and which is received by a photosensitive receiver.

It is necessary to test cigarettes for any faults, especially as regards a sufficient filling of tobacco, in conjunction with the packaging of the cigarettes. Conventionally, cigarette groups each assigned to a cigarette pack are tested before being enveloped in an inner wrapper (tin-foil blank). Cigarette groups or cigarette packs with at least one defective cigarette are separated out during the further packaging operation.

In a known device for testing cigarettes for faults by means of light, the light is directed towards the free end face of the cigarette. The relative arrangement here is such that the light reflected from the end face of the cigarette, namely the tobacco, is received by a receiver. If tobacco is missing in this region, light reflection cannot take place. The particular cigarette is identified as being defective. (German Offenlegungsschrift 3,201,666).

The testing of cigarettes for faults by means of light reflection is inaccurate because the fault signal is influenced solely by the state of the cigarette immediately in the region of the end face.

The object on which the invention is based is to propose measures for testing cigarettes or the like for faults, by means of which perfect and defective cigarettes can be identified quickly and reliably with the aid of simple test means.

To achieve this object, the process according to the invention comprises passing the light through at least a part region of the cigarette (transmitted-light process).

Accordingly, in the process of the invention, some of the light passes through the cigarette or through its envelope (cigarette paper) when a cigarette is defective. In the preferred embodiment of this process, light is guided into the cigarette via its free end face and, in the event of a fault, is received via a laterally arranged receiver which is consequently directed towards the cigarette envelope (cigarette paper). The particular receiver is arranged adjacent to the end face of the cigarette and laterally next to it. In the event of a defective cigarette, namely when there is no tobacco or an insufficient density of tobacco in the region of the end face, light consequently enters the cigarette in a longitudinal direction and, because it is deflected and passes through the cigarette paper, is received by the receiver.

The fault testing according to the invention is appropriately carried out on cigarette groups each assigned to a cigarette pack. A device which is especially suitable for this purpose consists of a test head with a holder (housing) having a number of receivers corresponding to the number of cigarettes to be tested. Where cigarette groups having several layers of cigarettes are concerned, the latter are offset relative to one another, so that at least one end region of each cigarette is free to allow a receiver to be arranged appropriately. The test head or housing is made appropriately step-shaped on the side facing the cigarette group, so that the end regions facing it can fit into corresponding recesses in the test head.

The cigarettes can be tested by means of visible, especially diffuse light which is generated by individual lamps (filament lamps) or by a common light source. Alternatively, infrared light appropriate for short cycle times and therefore for extremely short tests is suitable.

The cigarette groups are supplied, in the formation corresponding to the cigarette pack, to a test station in pockets of a conveyor. In this test station, testing is carried out during a short standstill phase or advantageously during the conveying movement of the cigarette groups.

Further features of the invention relate to details of the test process and of the device.

Figure 4:
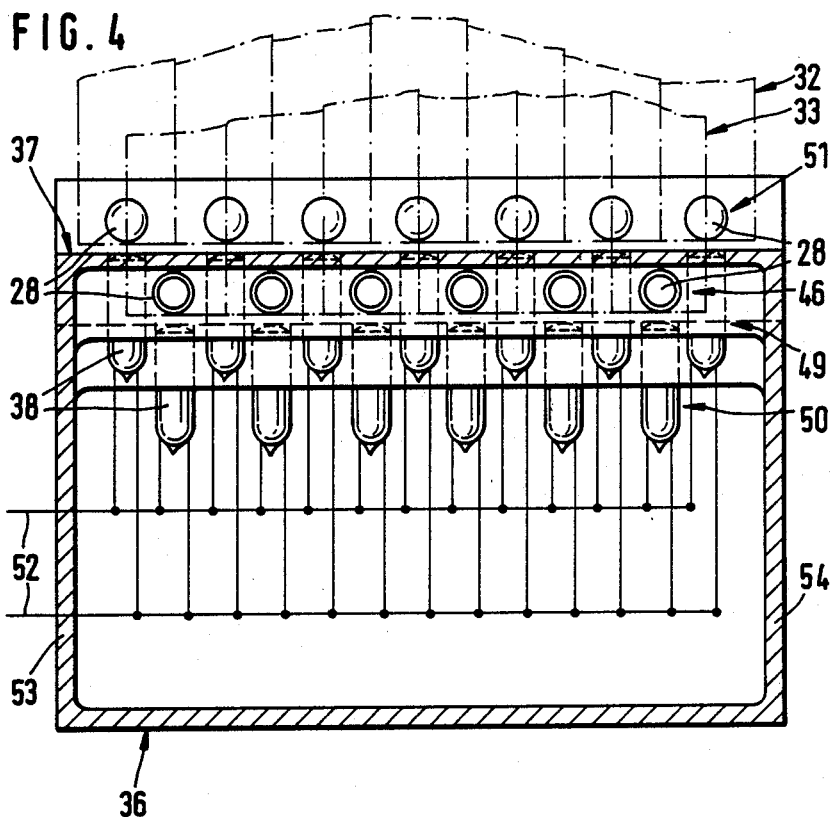
Figure 5:
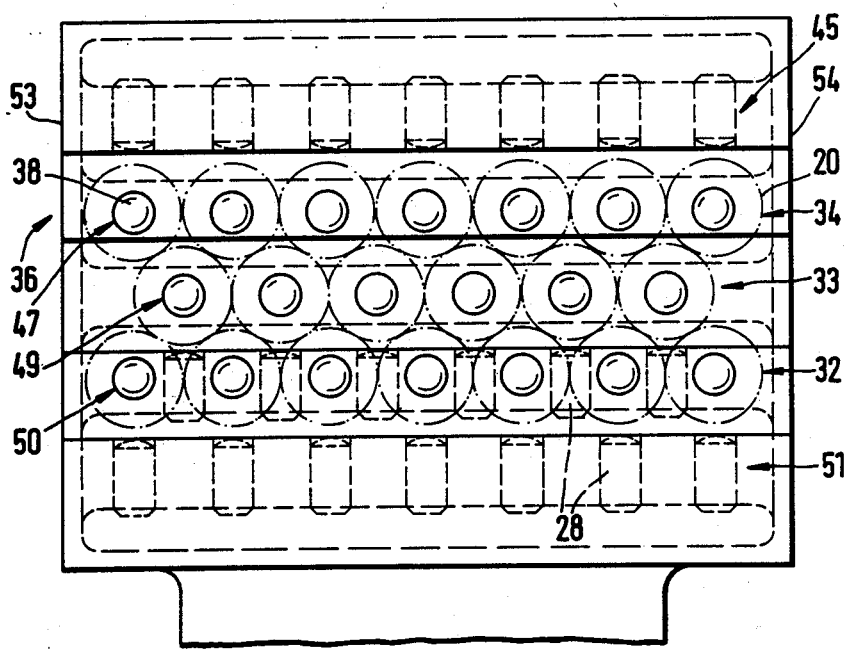
Figure 6:
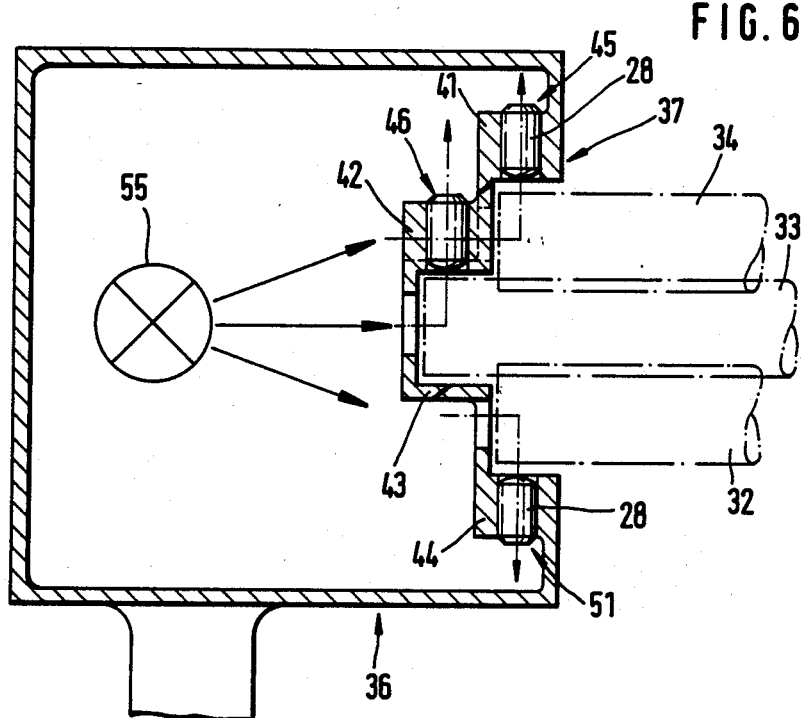
Figure 7:
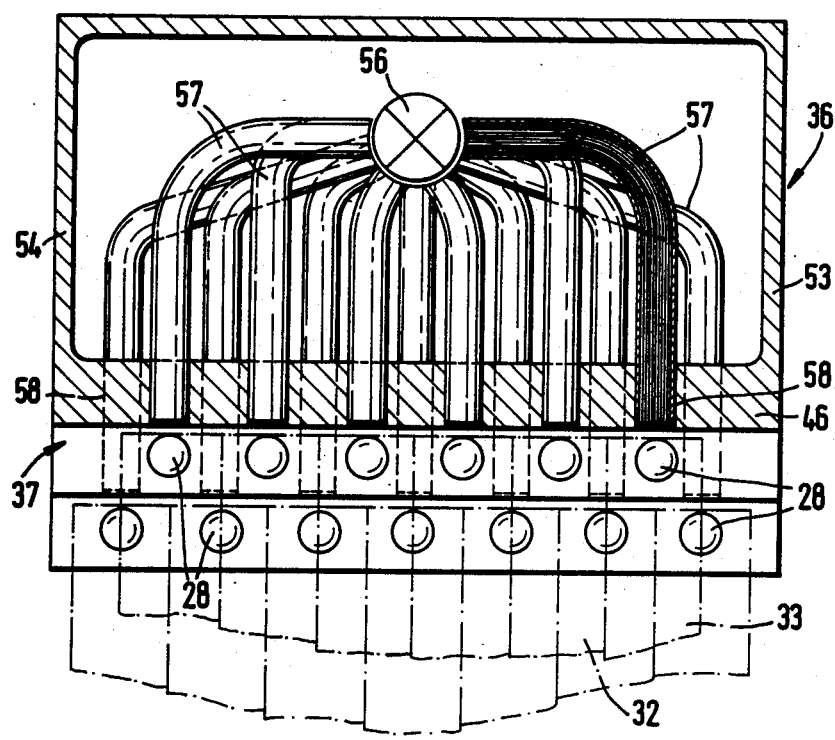
Figure 8:
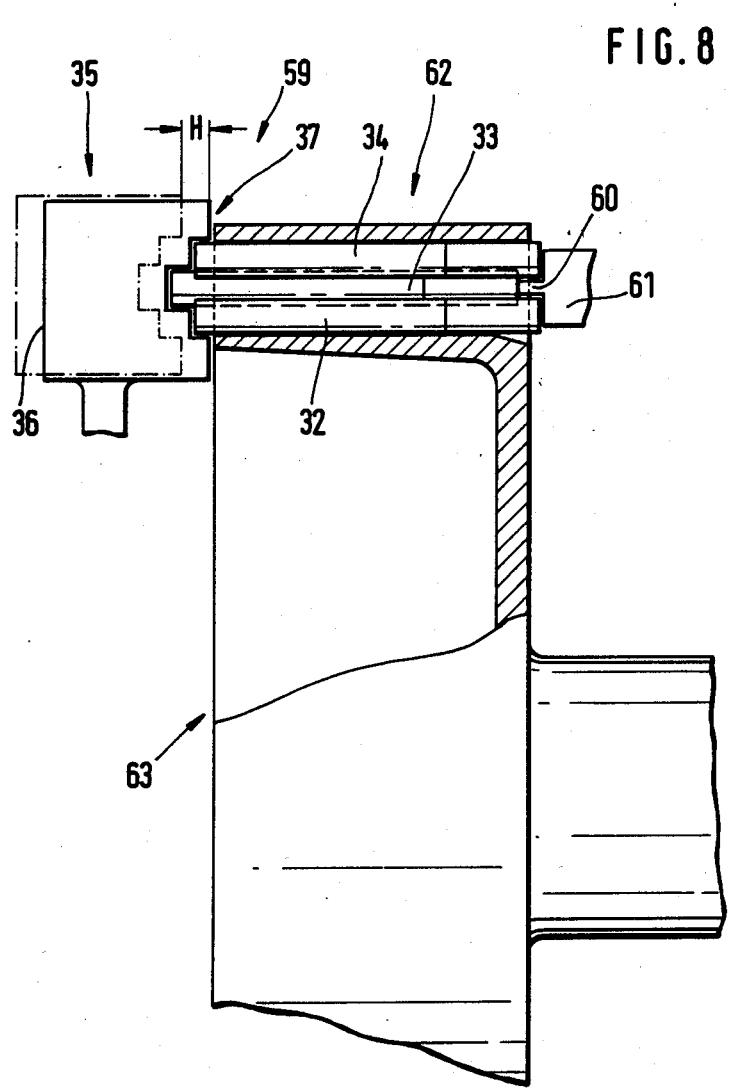
Figure 9:
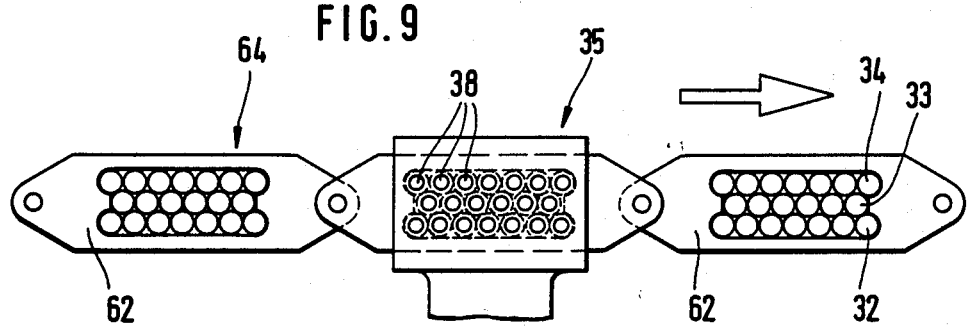
Figure 10:
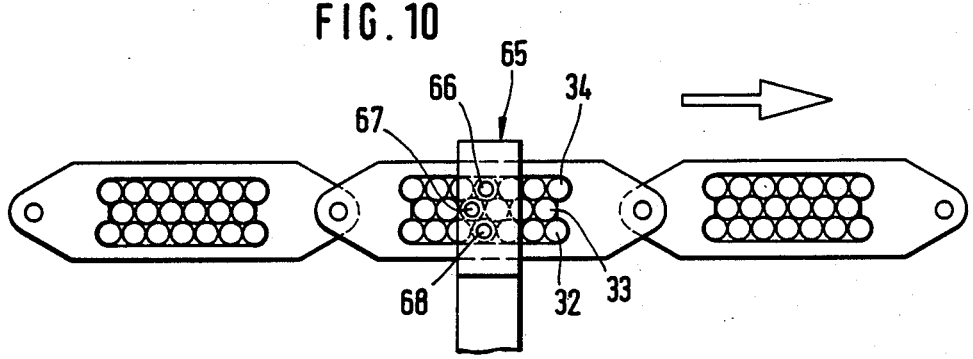

Exemplary embodiments of the device according to the invention are explained in more detail below with reference to the drawings in which:

FIG. 1 shows, in a side view and vertical section respectively, a diagrammatic representation of the operations involved in testing a defective cigarette, FIG. 2 shows a representation corresponding to FIG. 1, but relating to the testing of a proper cigarette, FIG. 3 shows a test device (test head) in a vertical section, FIG. 4 shows a horizontal section IV—IV of the test device according to FIG. 3, FIG. 5 shows a view V of the test device according to FIG. 3, FIG. 6 shows a representation corresponding to FIG. 3, and relating to another embodiment of the test head, FIG. 7 shows a further embodiment of a test head in a horizontal section, FIG. 8 shows part of a packaging machine (turret) with a test head, FIG. 9 shows a diagrammatic representation of part of a pocket chain as a conveyor for cigarette groups and with a test head, FIG. 10 shows, likewise in a diagrammatic side view, an alternative design of a test head for use in conjunction with a pocket chain.

The practical examples and exemplary embodiments illustrated in the drawings relate to the testing of cigarettes 20 (the so-called head check) before they are packaged.

FIGS. 1 and 2 illustrate diagrammatically the testing of cigarettes 20 with reference to a defective cigarette (FIG. 1) and with reference to a cigarette which is made properly (FIG. 2). These are cigarettes with a filter 21. Testing is carried out in the region of the end of the cigarettes 20 which is located opposite the filter 21. For this purpose, in the exemplary embodiment illustrated, light beams 22 are introduced into the cigarette 20 via an end face 23 in the longitudinal direction, that is to say in the axial direction. In the cigarette 20 according to FIG. 1, there is an incomplete filing of tobacco 24 in a region adjacent to the end face 23, in particular with a void 25 free of tobacco. The light beams 22 entering the cigarette 20, by being partially deflected to the side, generate light in the region of a cigarette envelope, namely in the cigarette paper 26. Deflection beams 27 pass through the cigarette paper 26 and because of the missing tobacco can be received here by a suitable receiver 28, especially a photodiode.

As regards the cigarette 20 in FIG. 2, which is properly filled with tobacco, there is no transverse deflection of light. On the contrary, the light is reflected or absorbed in the region of the end face 23.

The light signal received by the receiver 28 is suitably evaluated by machine, in such a way that the cigarette or a cigarette group or a cigarette pack, as the case may be, is separated out from the packaging cycle.

A diaphragm 29 located in front of the end faces 23 of the cigarettes 20 has a diaphragm aperture 30 which is centered on the end face 23 and which has, in the present case, a smaller diameter than this.

The testing of cigarettes 20 is appropriately carried out on cigarette groups 31. These consist of a number of cigarettes 20 corresponding to the finished cigarette packs and appropriately arranged in several, for example three layers 32, 33, 34. In the often customary formation illustrated here, the outer layers 32 and 34 consist of seven cigarettes and the middle layer 33 of six cigarettes. The latter are arranged in a "saddle position" in relation to the cigarettes of the outer layers 32 and 34.

A test head 35 consisting of a closed housing 36 serves for the (simultaneous) testing of the cigarettes 20 of a cigarette group 31 formed in this way. The necessary means for testing the cigarettes 20 are accommodated in a front wall 37 which faces the cigarettes 20 to be tested, of the housing 36. Electrical or electronic devices are located inside the housing 36.

In the exemplary embodiment of FIGS. 3 to 5, each cigarette 20 to be tested has assigned to it a separate receiver 28 which, as described, is directed transversely to its axis. Furthermore, each cigarette 20 has assigned to it a separate light source in the form of a small electric lamp 38. The lamps 38 designed, for example, as conventional signal lamps are suitably mounted in retaining bores 39 in the front wall 37 of the housing. Likewise, the (cylindrical) receivers 28 are mounted in transversely directed retaining bores 40 in the front wall 37.

For testing the cigarettes 20 of a cigarette group 31 consisting of more than two layers, the layers are offset relative to one another. In the present exemplary embodiment, the middle layer 33 is offset relative to the outer layers 32 and 34 in the manner of steps in the direction of the test head 35. As a result, the end regions of the cigarettes 20 of the middle layer 33 are likewise exposed, so that the associated receivers 28 can be arranged adjacent to the ends of these cigarettes.

The front wall 37 of the housing 36 is made step-shaped to match the offset arrangement of the end regions of the cigarettes 20. The wall steps 41, 42, 43 and 44 obtained as a result serve for accommodating transmitters (lamp 38) and/or receivers 28, the wall steps 41 to 44 being correspondingly thicker, in each case in the region where one component or the other is accommodated, than the remaining part of the housing 36.

In particular, an upper wall step 41 serves for accommodating the (vertically directed) receivers 28 of a row of receivers for the upper layer 34. The next wall step 42 set back inwards serves both for accommodating a further row of receivers 46 and for accommodating a row of lamps 47. The receivers 28 and the lamps 38 are mounted, in the region of this wall step 42, in retaining bores 39 and 40 located next to one another and having longitudinal axes offset 90° relative to one another.

Formed on the inside of the front wall 37, in the region of the middle layer 33, is a rib-like extension 48 which serves for mounting a row of lamps 49 in corresponding retaining bores 39. The following wall steps 43 and 44 serve for accommodating a further row of lamps 50 and a row of receivers 51 respectively. Accordingly, the receivers 28 of the lower row of receivers 51 act in an opposite direction (downwards) to the receivers of the upper row of receivers 40.

In this embodiment, the lamps 38 are supplied with current in a parallel connection via current leads 52.

The offsets in the front wall 37 of the housing 36 which are formed by the wall steps 41 to 44 are open on the sides, so that a continuous stepped recess is formed over the entire length or width of the housing 36 and also continues in the region of side walls 53, 54 of the housing.

The embodiment according to FIG. 6 differs from that described above in that, here, a common light source in the form of a central lamp 55 is arranged within the housing 36. The (diffuse) light generated by this is guided to the end faces 23 of the cigarettes 20 via diaphragm apertures 30 in the front wall 37. Even here, the front wall 37 of the housing 36 is made step-like in a similar way to the exemplary embodiment of FIGS. 3 to 5, with wall steps 41 to 44 of corresponding design and corresponding function. However, there are no receptacles for the separate lamps 38.

A special exemplary embodiment as regards the light source and light guidance is illustrated in FIG. 7 in a horizontal section through the housing 36 in the region of the smallest cross-section. Light emerging from a central lamp 56 is supplied via separate light guides 57, especially glass-fiber cables, to each individual cigarette 20 or to each end face 23 of the latter. The light guides 57 are each deflected arcuately according to requirements. The angle of deflection is not greater than 90°. The light guides 57 starting in the region of the central lamp 56 end in light-guide bores 58 in the front wall 37, specifically in the region of the wall steps 41 to 44. The diameter of the light-guide bores 58 corresponds to the outside diameter of the light guides 57. These terminate flush with the outer surface of the respective wall step 41 to 44. This embodiment corresponds to those already described as regards the arrangement of the receivers 28 in individual rows of receivers 45, 46 and 51.

Instead of light sources emitting visible light, other designs are also advantageous, especially using infrared light, the latter being especially advantageous for short work cycles.

The cigarettes 20 or cigarette groups 31 are appropriately supplied in succession to a test station 59 by means of a conveyor. The test device, namely the test head 35, is attached fixedly in this test station, in such a way that to conduct the test the test head 35 can be advanced by means of a short stroke to the particular cigarette group 31 to be tested (FIG. 8). Moreover, in the region of this test station 59, the relative position of the cigarettes 20 within the cigarette group 31 is temporarily changed by shifting the layers 32, 33 and 34 out of alignment. In the exemplary embodiment of FIG. 8, there is for this purpose a ram 61 which is step-shaped, in particular designed with a projection 60, and which is brought up against the cigarettes 20 on the side of these located opposite the test head 35 (against the filter 21) and thereby displaces the initially aligned cigarettes 20 relative to one another in the way described. In a station following the test station 59, the original aligned relative position of the cigarettes 20 can be restored, preferably by means of a counter-slide (not shown) which is effective on the same side as the test head 35.

The cigarette group 31 is received in individual pockets 62 of a preferably endless conveyor. In the exemplary embodiment of FIG. 8, these pockets 62 are arranged on the outer periphery of a revolving turret 63.

An alternative to this is illustrated in FIG. 9. Here, the pockets 62 are links of a pocket chain 64 acting as a conveyor. The pocket chain is designed in a known way so that the cigarette group 31, because of its special formation, is received positively in the pocket 62.

Here, the test head 35 is arranged laterally next to the path of movement of the pocket chain 64 and can be advanced by means of a lateral stroke to the particular cigarette group 31 to be tested. The test head 35 is designed, here, according to one or other of the exemplary embodiments described. The cigarettes 20 can be tested during a momentary brief standstill of the pocket chain, but alternatively also during continued (uniform) movement. In the latter case, the fixed test head 35 is sensitized briefly in such a way that the light signal, preferably infrared light, is emitted when the cigarettes 20 of the cigarette group 31 are momentarily co-ordinated with the test means (lamp, etc.) of the test head.

In the embodiment according to FIG. 10, a special test head 65 which simply has a number of cigarette-testing means corresponding to the number of layers 32, 33, 34 is used. These can be, in particular, the test means described in relation to FIGS. 3 to 7. The test head 65 can likewise be designed with a step-like front wall. Three transmitters 66, 67, 68 (and corresponding receivers) are arranged at the height of the layers 32, 33, 34, specifically offset relative to one another in the conveying direction, so that the transmitters 66, 67, 68 are each located opposite a cigarette of the three layers 32, 33, 34 simultaneously. Consequently, here, the cigarettes of the individual layers are tested in succession. This test process is appropriately carried out during the continuous movement of the pocket chain 64, the transmitters 66 to 68 being activated briefly and in synchronism with the movement of the cigarette group 31, so that all the cigarettes are sensed optically in succession.

We claim:

1. A testing device for testing the tobacco content of a cigarette comprising:
    a light source means for directing light to the cigarette under test;
    light receiver means for receiving the light from said light source means which enters said cigarette, is transmitted through at least a portion of said cigarette, and exits said cigarette from other than the points where the light enters the cigarette;
    test head means for receiving the cigarette under test such that light from said light source means is directed to an end face of said cigarette, said test head means including light receiver retaining means for locating and retaining said light receiver means at an angle to the longitudinal axis of said cigarette;
    said light receiver means including a plurality of light receivers and said test head means including means for receiving a plurality of cigarettes to receive light from said light source means and for holding a plurality of light receivers.

2. The testing device for testing the tobacco content of a cigarette as claimed in claim 1 wherein said test head means locates said light receiver means transverse to the longitudinal axis of said cigarette and adjacent said end face.

3. The testing device for testing the tobacco content of a cigarette as claimed in claim 1 wherein said test head means includes a diaphragm with a diaphragm aperture, said diaphragm being located in front of said cigarette end face receiving the light from said light source means, said diaphragm aperture having an area smaller than the area of said cigarette end face.

4. The testing device for testing the tobacco content of a cigarette as claimed in claim 1 wherein said light source means comprises a plurality of separate light sources equal in number to the number of cigarettes capable of being received by said test head means, said test head means further including means for retaining said plurality of light sources and for directing the light from said light sources to a respective one of the cigarettes received by said test head means.

5. The testing device for testing the tobacco content of a cigarette as claimed in claim 1 wherein said test head means is constructed to receive said plurality of cigarettes in plural layers.

6. The testing device for testing the tobacco content of a cigarette as claimed in claim 5 wherein said test head means is constructed to receive said plurality of cigarettes in several layers with the end faces of a cigarette in at least one layer extending beyond the end face of a cigarette in an adjacent layer.

7. The testing device for testing the tobacco content of a cigarette as claimed in claim 6 wherein said test head means comprises a housing having a step-shaped wall each step defining the position of a layer for receiving at least one cigarette.

8. The testing device for testing the tobacco content of a cigarette as claimed in claim 7 wherein each step of said step-shaped wall is provided with at least one first bore for locating and retaining a respective light receiver.

9. The testing device for testing the tobacco content of a cigarette as claimed in claim 8 wherein said light source means comprises a plurality of light sources and each step of said step-shaped wall further includes at least one second bore for holding a respective light source.

10. The testing device for testing the tobacco content of a cigarette as claimed in claim 1 wherein said light source means comprises a single light source and light guides for directing light from said single light source to said means for receiving a plurality of cigarettes such that each cigarette capable of being received by said test head means will receive light from said single light source.

11. The testing device for testing the tobacco content of a cigarette as claimed in claim 1 further including conveyer means for conveying groups of cigarettes to said test head means.

12. The testing device for testing the tobacco content of a cigarette as claimed in claim 11 wherein each group of said groups of cigarettes is arranged in a plurality of layers, further including means for extending the end faces of cigarettes in one layer beyond the end faces of cigarettes in its adjacent layers.

13. The testing device for testing the tobacco content of a cigarette as claimed in claim 1 wherein said light source means produces infrared light.

14. The testing device for testing the tobacco content of a cigarette as claimed in claim 1 wherein said light source means produces visible light.

* * * * *